(12) United States Patent
Friderich et al.

(10) Patent No.: US 6,767,852 B2
(45) Date of Patent: Jul. 27, 2004

(54) STRETCH EDGE ELASTIC LAMINATE

(75) Inventors: S. Scott Friderich, Alpharetta, GA (US); Leslie D. Dobbins, Marietta, GA (US); Lavada Campbell Boggs, Marietta, GA (US); James R. Fitts, Jr., Gainesville, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 136 days.

(21) Appl. No.: 09/751,407

(22) Filed: Dec. 28, 2000

(65) Prior Publication Data

US 2002/0086602 A1 Jul. 4, 2002

(51) Int. Cl.[7] .............................................. D04H 1/00
(52) U.S. Cl. ...................... 442/329; 428/192; 428/193
(58) Field of Search ................................ 428/192, 193; 442/329, 366, 381; 604/358, 385.22, 385.26

(56) References Cited

U.S. PATENT DOCUMENTS

| | | | |
|---|---|---|---|
| 3,338,992 A | 8/1967 | Kinney | 264/441 |
| 3,341,394 A | 9/1967 | Kinney | 442/366 |
| 3,502,538 A | 3/1970 | Petersen | 428/359 |
| 3,502,763 A | 3/1970 | Hartmann | 264/555 |
| 3,542,615 A | 11/1970 | Dobo et al. | 156/181 |
| 3,692,618 A | 9/1972 | Dorschner et al. | 442/401 |
| 3,802,817 A | 4/1974 | Matsuki et al. | 425/66 |
| 3,849,241 A | 11/1974 | Butin et al. | 428/137 |
| 3,985,599 A | 10/1976 | Lepoutre et al. | 156/164 |
| 4,300,562 A | 11/1981 | Pieniak | 604/385.26 |
| 4,340,563 A | 7/1982 | Appel et al. | 264/518 |
| 4,346,142 A | 8/1982 | Lazear | 428/315.7 |
| 4,477,506 A | 10/1984 | Wang | 428/172 |
| 4,484,971 A | 11/1984 | Wang | 156/244.14 |
| 4,720,415 A | 1/1988 | Vander Wielen et al. | 428/152 |
| 4,965,122 A | 10/1990 | Morman | 442/328 |
| 4,981,474 A | 1/1991 | Bopp et al. | 604/133 |
| 5,114,781 A | 5/1992 | Morman | 428/198 |
| 5,236,430 A | 8/1993 | Bridges | 604/396 |
| 5,335,675 A | 8/1994 | Wheeler et al. | 128/842 |
| 5,385,775 A | 1/1995 | Wright | 442/183 |
| 5,393,599 A | 2/1995 | Quantrille et al. | 442/57 |
| 5,419,795 A | 5/1995 | Wood et al. | 156/184 |
| 5,589,520 A | 12/1996 | Merz et al. | 521/64 |
| 5,614,297 A | 3/1997 | Velazquez | 428/212 |
| 5,635,290 A | 6/1997 | Stopper et al. | 428/198 |
| 5,681,302 A * | 10/1997 | Melbye et al. | 604/385.22 |
| 5,690,627 A | 11/1997 | Clear et al. | 604/385.29 |
| 5,733,822 A | 3/1998 | Gessner et al. | 442/35 |
| 5,804,286 A | 9/1998 | Quantrille et al. | 428/198 |
| 5,861,442 A | 1/1999 | Merz et al. | 521/64 |
| 5,910,224 A | 6/1999 | Morman | 156/178 |
| 6,001,303 A | 12/1999 | Haynes et al. | 264/555 |
| 6,057,024 A | 5/2000 | Mleziva et al. | 428/114 |

FOREIGN PATENT DOCUMENTS

WO     WO 95/34264     12/1995

* cited by examiner

*Primary Examiner*—Terrel Morris
*Assistant Examiner*—A B Sperty
(74) *Attorney, Agent, or Firm*—Pauley Petersen & Erickson

(57) ABSTRACT

A stretch edge elastic laminate having a plurality of elastic filaments substantially aligned in a machine direction and forming an elastic zone and at least one stretch edge positioned along a first lateral edge region of the stretch edge elastic laminate forming a first gasket zone. Desirably, an opposing second stretch edge is positioned along a second lateral edge region of the stretch edge elastic laminate to form a second gasket zone. A nonwoven facing material is bonded to at least one side of the elastic layer.

23 Claims, 4 Drawing Sheets

STRETCH EDGE ELASTIC LAMINATE

BACKGROUND OF THE INVENTION

Garments, including pant-like absorbent garments, medical garments, and other products, are commonly made with an elastic containment feature adjacent at least one of the garment openings. A pant-like garment, for instance, may have an elastic containment feature adjacent the waist opening, each of the two leg openings, or all three of the openings. The elastic containment features are intended to fit snugly around a wearer's body to serve as gaskets, which prevent or reduce leakage of waste materials from inside the garment. Elastic containment features have also been employed in leg flaps that provide further leakage protection in pant-like garments, and in other auxiliary gasketing applications.

Many conventional elastic containment features are made of a folded web with a high propensity to ruffle and buckle during use. As a result of ruffling, the gasketing and containment characteristics around the openings in the garment are compromised and leakage occurs.

Thus, there is a need or desire for an elastic laminate for use as an elastic containment feature in garments which provides a consistent gasket to reduce ruffling and prevent or reduce leakage.

There is also a need or desire for an elastic laminate for use in an elastic containment feature which provides for a more attractive fit around the openings of the garment, for example the waist and leg openings.

SUMMARY OF THE INVENTION

In response to the discussed difficulties and problems encountered in the prior art, a stretch edge elastic laminate ("SEEL"), has been discovered. The SEEL has at least one elastic filament layer having a plurality of elastic filaments, desirably thermoplastic filaments, aligned in a machine direction and forming an elastic zone or region and at least one gasket zone or region defined by a stretch edge aligned in the machine direction. The elastic filament layer is positioned adjacent to one or two facing layers. An elastic film or plug is located adjacent to the facing layer(s) at one or both side edges of the laminate. The stretch edge is defined by the elastic film or plug and the facing layer(s) at one or both edges.

Suitable polymer or polymer blends used to prepare the elastic filaments and the elastic film or plug include olefin polymers, such as an olefinic copolymer of polyethylene. More specifically, other suitable polymers include diblock, triblock, tetrablock or other multi-block elastomeric copolymers such as olefinic copolymers. The elastic filaments and the elastic film or plug may also contain blends of elastic and inelastic polymers, or of two or more elastic polymers, provided that the blend exhibits elastic properties.

The elastic filaments may be made of a first elastomer or elastomer blend, and the elastic film or plug may be made of the same or a different elastomer or elastomer blend, having different tensile properties than the first elastomer or elastomer blend. In another embodiment, the elastic filaments may be a first elastomer and the elastic film or plug may be an elastomer blend having a different percentage amount of the first elastomer, with an added non-elastic component, making the modulus of the second elastomer blend greater than the modulus of the first elastomer.

In another embodiment, the elastic film or plug may be a blend of elastomers, for example KRATON® styrene-ethylene/propylene rubber and a polyethylene elastomer, having a modulus and/or basis weight (and, thus, tension) greater than a modulus and/or basis weight of a first elastomer used to form elastic filaments. The polyethylene is added to increase the modulus for the elastomeric film or plug.

Desirably, a first elastic film or plug is positioned along a first lateral edge portion of the SEEL and substantially aligned in the machine direction and a second elastic film or plug is positioned at an opposing second edge portion of the SEEL and substantially aligned in the machine direction. The elastic filaments are positioned within the elastic layer, between the first elastic film or plug and the second elastic film or plug. Desirably, each elastic film or plug has a width of about 0.078 inch to about 0.236 inch, more desirably about 0.118 inch.

The polymer or polymer blend used to make the elastic filaments may have a different tension (i.e., exhibits different retractive force when stretched) than the polymer or polymer blend used to make the elastic film or plug. Thus, the elastic zone may have a first tension and the gasket zone may have a second tension different from the first tension. Desirably, but not necessarily, the second tension is equal to or greater than the first tension.

A first facing material is bonded to a first side of the elastic layer and an opposing second facing material can be bonded to a second side of the elastic filament layer. Each of the facing materials desirably is a nonwoven web, formed using conventional web forming processes. The first facing material and the second facing material may be made of the same or similar material or different material. Additionally, a barrier film, desirably a polymer film such as a polyethylene film, can be positioned between the elastic layer and the first facing material and/or the second facing material.

The SEEL in accordance with this invention may be made or produced, for example using a continuous vertical filament laminate ("VFL") method. Other suitable processes, for example a continuous filament spunbond laminate ("CFSBL") process, may be used to produce the SEEL material in accordance with this invention. Molten elastomeric material may be extruded from a first spin plate region as a plurality of elastomeric filaments. Similarly, a wide elastic member may be extruded from a second spin plate region through a rectangular slot. The resulting elastic layer may have a higher elastic tension and/or lower stretch in the gasket zone, due to the wide elastic member, than in the elastic zone, which contains the elastic filaments. After extruding, the elastic filaments and the wide elastic member are quenched and solidified and then stretched or elongated. The elastic filaments and the wide elastic member can be stretched by about 100% to about 800% of an initial length, desirably by about 200% to about 700% of an initial length.

Before or after the elastic filaments and the wide elastic member are stretched, the elastic layer is laminated to the first facing material and/or a second facing material. The laminate material is then bonded and is relaxed and/or retracted to produce the SEEL. The laminate material can then be slit or cut through a general centerline of each wide elastic member to form a corresponding elastic film or plug positioned along each lateral edge portion or region of the SEEL. The wide elastic member can be slit or cut using any conventional slitting or cutting means known to those having ordinary skill in the art. As a result of the slitting of each wide elastic member, the SEEL will have a continuous gasket zone, defined by the elastic film or plug, positioned along each lateral edge portion or region. Alternatively, if the wide elastic member is positioned at the edge(s) of the laminate prior to cutting, the laminate need not be cut to form the stretch edge.

The invention encompasses various types of garments or absorbent articles in which a gasket zone is present in the vicinity of any one or more garment openings. Depending on the garment, gasket zones may encircle an entire garment opening or just a portion of the garment opening. Types of garments on which this invention can be used include personal care garments, such as diapers, training pants, absorbent underpants, adult incontinence products, certain feminine hygiene articles, and swim wear, as well as in medical garments.

With the foregoing in mind, it is a feature and advantage of the invention to provide a stretch edge elastic laminate having a continuous gasket zone with elastic properties positioned along at least one lateral edge region of the laminate material.

It is also a feature and advantage of the invention to provide a stretch edge elastic laminate having an elastic zone and a gasket zone with different tension and/or elastic properties.

DEFINITIONS

Figure 1:
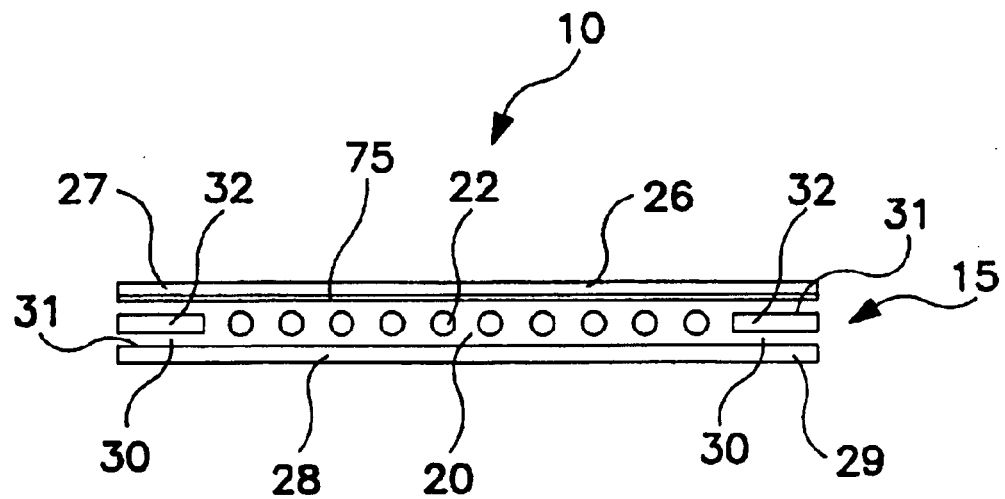
FIG. 1 is a schematic sectional view of a stretch edge elastic laminate ("SEEL") material having an elastic zone and at least one gasket zone, in accordance with one embodiment of this invention.

The term "stretch edge" refers to an edge portion or region of a laminate which includes a first facing layer, an optional second facing layer, a web of elastic filaments adjacent to the facing layer(s), and an elastic film or plug adjacent to the facing layer(s) at one or both edges (i.e. extending all the way to one or both edge boundaries) of the laminate. The stretch edge (and corresponding elastic film or plug) desirably has a width of about 0.078 inch to about 0.236 inch, more desirably about 0.118 inch. The elastic film or plug desirably has a thickness of about 0.003 inch to about 0.015 inch, and a width-to-thickness ratio of greater than about 5, more desirably greater than about 10, still more desirably about 15 to about 80. Filaments, by contrast, typically have a width-to-thickness ratio not more than about 2.

The term "vertical filament laminate" process or "VFL" process refers to one continuous process for making a SEEL material, as described herein.

The term "tension" and the term "elastic tension" refer to the amount of force per unit width required to stretch an elastic material (or a selected zone thereof) to a given percent elongation.

The term "nonwoven fabric or web" means a web having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "film" refers to a film made using a film extrusion and/or forming process, such as a cast film or blown film extrusion process.

The term "microfibers" means small diameter fibers having an average diameter not greater than about 75 microns, for example, having an average diameter of from about 1 micron to about 50 microns, or more particularly, having an average diameter of from about 1 micron to about 30 microns.

The term "spunbond fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. Nos. 4,340,563 to Appel et al., 3,692,618 to Dorschner et al., 3,802,817 to Matsuki et al., 3,338,992 and 3,341,394 to Kinney, 3,502, 763 to Hartman, 3,502,538 to Petersen, and 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

The term "meltblown fibers" means fibers formed by extruding a molten thermoplastic material through a plurality of fine, usually circular, die capillaries as molten threads or filaments into converging high velocity gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. Nos. 3,849,241 to Butin and in 6,001,303 to Haynes, et al. Meltblown fibers are microfibers which may be continuous or discontinuous and are generally self bonding when deposited onto a collecting surface.

The term "polymer" generally includes but is not limited to, homopolymers, copolymers, including block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "substantially continuous filaments or fibers" refers to filaments or fibers prepared by extrusion from a spinnerette, including without limitation spunbond and meltblown fibers, which are not cut from their original length prior to being formed into a nonwoven web or fabric. Substantially continuous filaments or fibers may have lengths ranging from greater than about 15 cm to more than one meter; and up to the length of the nonwoven web or fabric being formed. The definition of "substantially continuous filaments or fibers" includes those which are not cut prior to being formed into a nonwoven web or fabric, but which are later cut when the nonwoven web or fabric is cut.

The term "thermoplastic" is meant to describe a material that softens when exposed to heat and which substantially returns to its original condition when cooled to room temperature.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 25 percent greater than its relaxed unbiased length, and that will cause the material to recover at least 40 percent of its elongation upon release of the stretching elongating force. A hypothetical example which would satisfy this definition of an elastomeric material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, and many of these will recover to substantially their original relaxed length upon release of the stretching, elongating force. This latter class of materials is generally beneficial for purposes of the present invention.

The term "elongation" refers to the capability of a material to be stretched a certain distance, such that greater elongation refers to a material capable of being stretched a greater distance than a material having lower elongation.

The term "recover" or "retract" relates to a contraction of a stretched material upon termination of a biasing force following stretching of the material by application of the biasing force.

The term "personal care absorbent garment" includes disposable diapers, training pants, swim wear, absorbent underpants, adult incontinence products, and feminine hygiene products.

The term "protective garment" includes protective (i.e., medical and/or industrial) disposable gowns, caps, gloves, drapes, face masks, and the like.

The term "disposable garment" includes personal care absorbent garments and protective garments.

The term "inelastic" refers to materials that are not elastic.

"Inward" and "outward" refer to positions relative to the center of an article, and particularly transversely and/or longitudinally closer to or away from the longitudinal and transverse center of the article.

DETAILED DESCRIPTION OF THE PRESENTLY PREFERRED EMBODIMENTS

The principles of this invention can be applied to a wide variety of garments, including disposable absorbent articles, having a gasket zone in the vicinity of at least one article opening, for example a leg opening and a waist opening. Examples of absorbent articles include diapers, training pants, certain feminine hygiene products, adult incontinence products, other personal care or medical garments, and the like.

Referring to FIG. 1, a stretch edge elastic laminate ("SEEL") material, in accordance with one embodiment of this invention, includes at least one elastic layer 15 and at least one elastic zone or region 20 and at least one gasket zone or region 30. The elastic zone or region 20 is made of a plurality of elastic filaments 22, desirably thermoplastic filaments, substantially aligned in a machine direction and laminated to one or two facing layer(s) or materials 26 and 28. The gasket zone or region 30 is formed or defined by one or two stretch edge(s) 31 positioned along a length of the lateral edge region of the SEEL material and substantially aligned in a machine direction. The gasket zone 30 exhibits a moderate level of elastic tension against the wearer's body during use, and restricts the flow of liquid and other material through a garment opening between the inside and outside of the garment. Desirably, the SEEL material has a continuous gasket zone 30 positioned along each lateral edge region 27, 29. Each stretch edge 31 includes an elastic film or plug 32 laminated directly or indirectly (i.e. with or without intervening layer(s)) to one or two facing layers or materials 26, 28. Desirably, the elastic film or plug 32 is laminated or bonded to a lateral edge of the facing material 26, 28, as shown in FIG. 1.

In one embodiment of this invention, at least one elastic layer 15 includes a plurality of elastic filaments 22 in a central region of the elastic layer 15 and an elastic film or plug 32 in at least one lateral edge region of the elastic layer 15. The first facing material 26 is bonded to a first side of the elastic layer 15 and the second facing material 28 is bonded to a second side of the elastic layer 15 so that a lateral edge of the elastic film or plug 32 is aligned with a lateral edge of each of the first and second facing materials 26, 28, as shown in FIG. 1.

The stretch edge 31 can be formed by cutting or slitting a laminate including a wide elastic member 24, using methods discussed below with respect to FIGS. 3 and 4. Desirably, the wide elastic member 24 has a width of at least about 0.156 inch, more desirably at least about 0.236 inch and is positioned along a length of the lateral edge region(s) 27, 29 of the SEEL material. The wide elastic member 24 may be narrower, provided that it can be effectively cut lengthwise to form the stretch edge 31. If the elastic film or plug 32 is initially positioned at an edge of the laminate, then the forming and cutting of a longer wide elastic member 24 may not be required.

In accordance with one embodiment of this invention, the elastic filaments 22 have a generally circular cross-sectional shape. The elastic filaments 22 may have any other suitable shape. Desirably, the elastic filaments 22 each have a thickness and a width of about 0.011 inch to about 0.019 inch, more desirably a thickness and a width of about 0.015 inch. Thus, the elastic filaments 22 each have a width-to-thickness ratio of not more than about 2, more desirably about 1. Additionally, the elastic filaments 22 desirably have a denier range of about 250 to about 1100, more desirably about 300 to about 600. Desirably, the elastic filaments 22 making the elastic zone 20 exhibit a stretch of at least about 25%, more desirably at least about 50%.

Suitable polymer or polymer blends used to prepare the elastic filaments 22 and the elastic film or plug 32 herein include olefin polymers, such as an olefinic copolymer of polyethylene. More specifically, other suitable polymers include diblock, triblock, tetrablock or other multi-block elastomeric copolymers such as olefinic copolymers, including styrene-isoprene-styrene, styrene-butadiene-styrene, styrene-ethylene/ butylene-styrene, or styrene-ethylene/ propylene-styrene, which may be obtained from Kraton Inc., under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having a density less than about 0.89 grams/cc, available from Dow Chemical Co. under the trade name AFFINITY®.

The elastic filaments 22 and the elastic film or plug 32 may also contain blends of elastic and inelastic polymers, or of two or more elastic polymers, provided that the blend exhibits elastic properties. The elastic filaments 22 and the elastic film or plug 32 may be substantially continuous or of specific length, but are desirably substantially continuous. Substantially continuous filaments have better elastic recovery than shorter filaments. The elastic filaments 22 may be circular but may also have other cross-sectional geometries such as elliptical, rectangular, triangular or multi-lobal. In one embodiment, the elastic film or plug 32 is formed as an elongated, rectangular film or plug produced from a film extrusion die having at least one slotted opening.

In accordance with one embodiment of this invention, the elastic filaments 22 are made of a first elastomer composition and the elastic film or plug 32 is made of a second elastomer composition different from the first elastomer composition. For example, the elastic filaments 22 may be made of a first elastomer or elastomer blend, and the elastic film or plug 32 is made of a different elastomer or elastomer blend, having different tensile properties than the first elastomer or elastomer blend. In another embodiment, the elastic filaments 22 are made of a first elastomer and the elastic film or plug 32 is made of an elastomer blend having a different percentage amount of the first elastomer, with an added non-elastic component, making the modulus of the second elastomer blend greater than the modulus of the first elastomer. For example, the elastic film or plug 32 may have a styrene-ethylene/propylene rubber, such as a KRATON® styrene-ethylene/propylene rubber, as a base elastomer, and a polyethylene wax as a processing aid. The elastic filaments 22 may include styrene-ethylene/propylene rubber without the polyethylene wax, or with a lower amount of it. Various additives are known in the art which may aid in processing and achieving desired properties.

In another embodiment, the elastic film or plug 32 is made of a blend of elastomers, for example KRATON® styrene-ethylene/propylene rubber and a polyethylene elastomer, having a modulus and/or basis weight (and, thus, tension) greater than a modulus and/or basis weight of a first elastomer used to form elastic filaments 22. The polyethylene is added to increase the modulus for the elastic film or plug 32.

Desirably, the elastic film or plug 32 is positioned within the elastic layer 15 and adjacent the plurality of elastic filaments 22. In accordance with one embodiment of this invention, the elastic film or plug 32 has a generally rectangular cross-sectional shape. Desirably, the elastic film or plug 32 has a width not greater than about 0.236 inch, desirably about 0.078 inch to about 0.236 inch, more desirably about 0.118 inch, and a thickness of about 0.003 inch to about 0.015 inch. Desirably, the elastic film or plug 32 has a width-to-thickness ratio of greater than about 5, more desirably greater than about 10, still more desirably about 16 to about 78. The elastic film or plug 32 is positioned along a first lateral edge region 27 of the SEEL 10 and substantially aligned in the machine direction. In accordance with one embodiment of this invention, a second elastic film or plug 32 is positioned at an opposing second edge region 29 of the SEEL 10 and substantially aligned in the machine direction, as shown in FIG. 1.

The polymer or polymer blend used to make the elastic filaments 22 may have a different tension (i.e., exhibits different retractive force when stretched) than the polymer or polymer blend used to make the elastic film or plug 32. Thus, the elastic zone 20 may have a first tension and the gasket zone 30 may have a second tension different from the first tension. A standard tensile test can be performed on the elastic zone 20 and the gasket zone 30 wherein load applied to the material is measured as a function of elongation using the standard testing method, ASTM-529W. At 90% elongation, the elastic zone 20 desirably has a first tension of at least about 40 g and the gasket zone 30 desirably has a tension of about 80 g to about 250 g. Desirably, but not necessarily, the second tension is equal to or greater than the first tension.

Elastic tension can be measured, for instance, using an MTS Sintec Model 1/s, available from MTS in Research Triangle Park, N.C., with a crosshead speed set to 500 mm/min. Samples having a 3-inch width and 6-inch length can be used, with 3 inches of the length clamped inside the jaws (leaving 3 inches of length for testing). The tension of each elastic zone 20 and gasket zone 30 can be measured after the portion of the SEEL 10 being tested is held in the extended condition (in the machine direction of the SEEL 10) for 60 seconds.

In one embodiment of this invention as shown in FIG. 1, at least one elastic zone 20 is laterally adjacent to at least one gasket zone 30. Desirably, one elastic zone 20 is laterally positioned between two gasket zones 30. In other embodiments of this invention, the elastic zone 20 and the gasket zone 30 are spaced apart from each other. In another embodiment of this invention, at least a portion of the elastic zone 20 overlaps at least a portion of the gasket zone 30.

As shown in FIG. 1, a first facing material 26 is bonded to a first side of the elastic layer 15. The SEEL 10 may also include an opposing second facing material 28 bonded to a second side of the elastic layer 15. Each of the first facing material 26 and the second facing material 28 may be a nonwoven web, for example a spunbond web or a meltblown web, a woven web, a film or laminates thereof. The first facing material 26 and the second facing material 28 may be formed using conventional processes, including the spunbond and meltblowing processes described in the above "DEFINITIONS." For example, the facing materials 26, 28 may be a spunbond web having a basis weight of about 0.1 osy to about 4.0 osy, desirably about 0.2 osy to about 2.0 osy, more desirably about 0.4 osy to about 0.6 osy. The first facing material 26 and the second facing material 28 may be made of the same or similar material or different material.

In one embodiment of this invention, the first facing material 26 and the second facing material 28 are bonded to the opposing sides of the elastic layer 15 with an adhesive, for example an elastomeric adhesive such as Findley H2525A or H2096, available from Bostik Findley. Other bonding means well known to those having ordinary skill in the art may also be used to bond the facing materials 26, 28 to the elastic layer 15, including thermal bonding, ultrasonic bonding, mechanical stitching and the like. In alternative embodiments, a tackifier may be included in one or more layers to improve thermal bonding or ultrasonic bonding. In one embodiment of this invention, a barrier film 75, desirably a polymer film such as a polyethylene film, is positioned between the elastic layer 15 and the first facing material 26 and/or the second facing material 28, as shown in FIG. 1.

Figure 2:
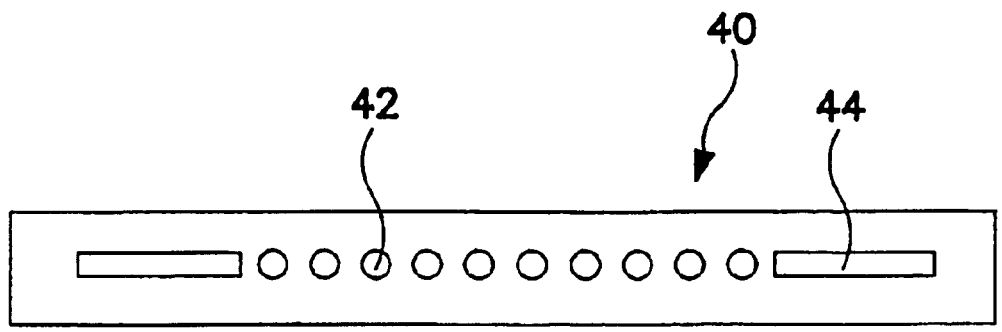
FIG. 2 is a schematic view of a die plate used to produce a SEEL material, in accordance with one embodiment of this invention.

FIG. 2 illustrates a die arrangement 40 useful for preparing the elastic layer 15. The die arrangement 40 has a plurality of spinning holes 42 for forming or extruding the elastic filaments 22 and two laterally opposing slots 44 each for forming or extruding a wide elastic member 24 arranged in a generally single row. Each slot 44 is generally rectangular in shape and the wide elastic member 24 which is formed or extruded through each slot 44 eventually forms a stretch edge 31, as discussed below. It is apparent to one having ordinary skill in the art that the elastic filaments 22 and the wide elastic members 24 may be extruded from different zones of a single die or die arrangement, or from two or more different dies. Each wide elastic member 24 desirably has a width which is about twice the width of the two elastic films or plugs 32 which can be formed when the wide elastic member 24 is cut along its length, as described below. In any event, the wide elastic member 24 must be wider than the elastic film or plug 32 even if the cutting of the wide elastic member 24 is not intended to form two elastic films or plugs 32.

Figure 3:
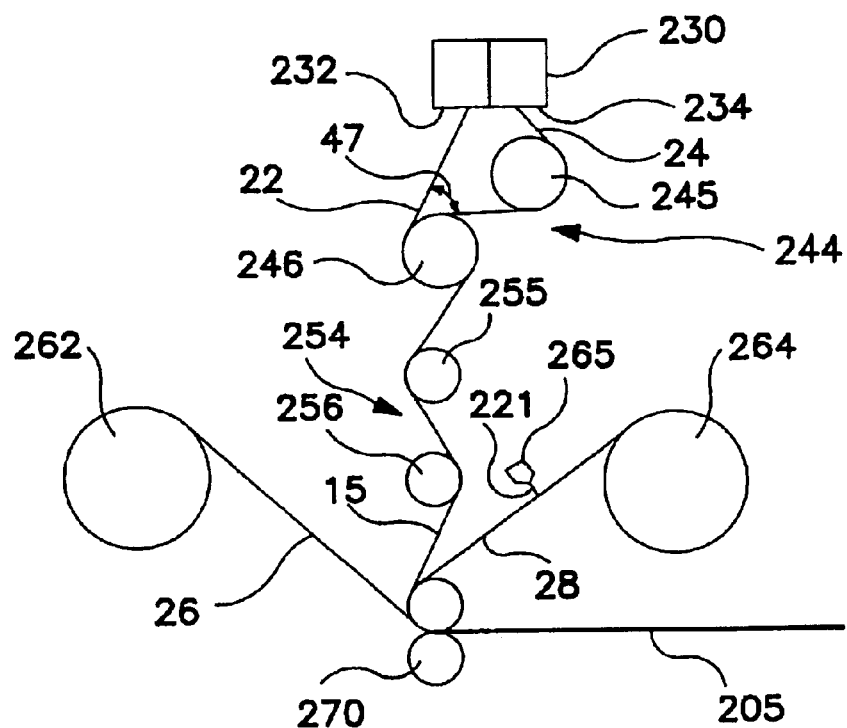
FIG. 3 is a schematic view of a vertical filament laminate ("VFL") process for producing a SEEL material, in accordance with one embodiment of this invention.
Figure 4:
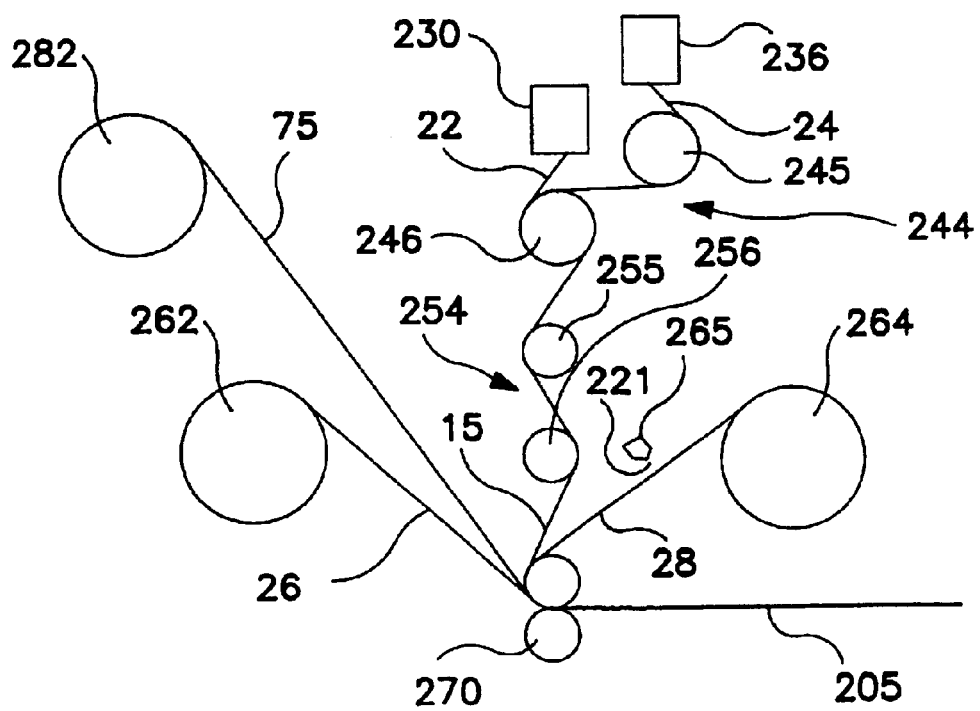
FIG. 4 is a schematic view of a vertical filament laminate ("VFL") process for producing a SEEL material, in accordance with one embodiment of this invention.

FIGS. 3 and 4 illustrate exemplary processes for making the SEEL 10 in accordance with one embodiment of this invention. FIGS. 3 and 4 each illustrates a continuous vertical filament laminate ("VFL") method. Alternative processes for making the SEEL 10 in accordance with embodiments of this invention, include for example a continuous filament spunbond laminate ("CFSBL") process as taught in U.S. Pat. Nos. 5,385,775 to Wright and 6,057,024 to Mleziva et al., the disclosures of which are incorporated herein by reference.

Referring to FIG. 3, a first extruder (not shown) supplies a first molten elastomeric polymer or polymer blend to a first die 230. The first die 230 includes different regions of spinning holes tailored to provide the elastic layer 15 having at least one elastic zone or region 20 and at least one gasket zone or region 30. Molten elastomeric material is extruded from a first spin plate region 232 through spinning holes 42 as a plurality of elastic filaments 22. Similarly, a wide elastic member 24 is extruded from a second spin plate region 234 through the rectangular slot 44. The resulting elastic layer 15 has a higher elastic tension and/or lower stretch in the gasket zone 30 defined by the wide elastic member 24, than in the elastic zone 20 defined by the elastic filaments 22. After extruding, the elastic filaments 22 and the wide elastic member 24 are quenched and solidified.

In accordance with one embodiment of this invention, the elastic filaments 22 and the wide elastic member 24 are quenched and solidified by passing them over a first series of chill rolls 244. For instance, the elastic filaments 22 may be contacted with chill roll 246. The wide elastic member 24 may be passed over two chill rolls 245 and 246. Desirably, chill rolls 245 and 246 have a temperature of about 40° F. to about 80° F.

After the elastic filaments 22 and the wide elastic member 24 are quenched and solidified, they are stretched or elongated. The elastic filaments 22 and the wide elastic member 24 are stretched using a first series of stretch rolls 254. The first series of stretch rolls 254 may include one or more individual stretch rolls 255, desirably at least two stretch rolls 255 and 256, as shown in FIG. 3. The stretch rolls 255 and 256 rotate at a speed greater than a speed at which the chill rolls 245 and 246 rotate, thereby stretching the elastic filaments 22 and the wide elastic member 24.

Desirably, each successive roll rotates at a speed greater than the speed of the previous roll. For example, referring to FIG. 3, the chill roll 245 rotates at a speed "x"; the chill roll 246 rotates at a speed greater than "x", for example about "1.1x"; the stretch roll 255 rotates at a still greater speed, for example about "1.1 5x"; the second stretch roll 256 rotates at a still greater speed, for example about "1.25x" to about "2x"; and a third stretch roll 257 rotates at a still greater speed, for example about "2x" to about "7x." As a result, the elastic filaments 22 and the wide elastic member 24 can be stretched by about 100% to about 800% of an initial length, desirably by about 200% to about 700% of an initial length.

After the elastic filaments 22 and the wide elastic member 24 are stretched, the elastic layer 15 is laminated to a first facing material 26 and/or a second facing material 28. The first facing material 26 is unwound from the roller 262 and laminated to a first side of the elastic layer 15. The second facing material 28 is unwound from the roller 264 and laminated to a second side of elastic layer 15. As shown in FIG. 3, before the second facing material 28 is laminated to a second side of elastic layer 15, at least a portion of second facing material 28 can be coated or sprayed with an elastomeric adhesive 221, for instance Findley H2525A or H2096 elastomeric meltblown adhesive, via an adhesive sprayer 265. The laminate material is then passed through nip rolls 270 (desirably smooth calender rolls) and is relaxed and/or retracted to produce the SEEL 10. Other means for bonding the laminate material known to those having ordinary skill in the art may be used in place of nip roll 270.

FIG. 4 illustrates a VFL process similar to that of FIG. 3. In FIG. 4, instead of using a single spinnerette 230 having adjacent die regions for the elastic zone 20 and the gasket zone 30, two spinnerettes 230 and 236 are employed. The first spinnerette 230 extrudes the elastic filaments 22. The second spinnerette 236 extrudes the wide elastic member 24. Additionally, an optional breathable barrier layer 75 is unwound from one of the rollers 282 and bonded between the first facing material 26 and the elastic layer 15. Except for the use of two spinnerettes instead of one "hybrid" spinnerette, and the optional breathable barrier layer 75, the processes of FIGS. 3 and 4 are similar. In either case, the elastic filaments 22 and the wide elastic member 24 ultimately converge to form a single elastic layer 15 having at least one elastic zone 20 and at least one gasket zone 30. The elastic filaments 22 and the wide elastic member 24 may converge in a spaced-apart fashion to produce the elastic zone 20 and the gasket zone 30.

Figure 5:
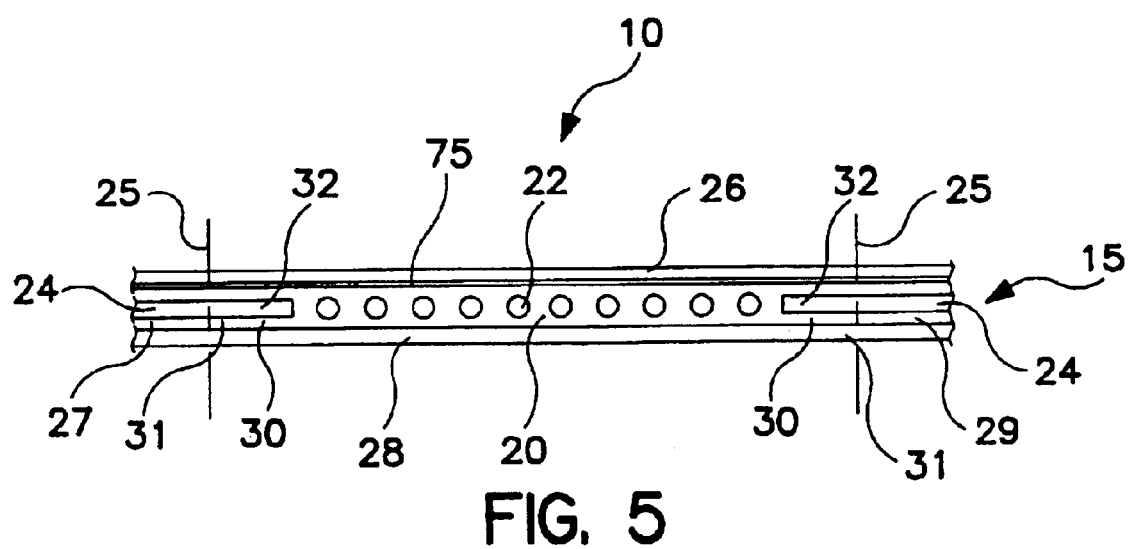
FIG. 5 is a schematic view of a SEEL material having laterally opposing wide elastic members which are subsequently slit to form corresponding continuous elastomeric film or plugs along each lateral edge region of the SEEL material, in accordance with one embodiment of this invention.

As shown in FIG. 5, after the laminate material is passed through the nip rolls 270 and allowed to relax and/or retract to form the SEEL 10, the SEEL 10 is slit or cut through a general centerline 25 of each wide elastic member 24 to form a corresponding stretch edge 31 (including elastic film or plug 32) positioned along each lateral edge region 27, 29 of the SEEL 10. The laminate including the wide elastic member 24 can be slit or cut using any conventional slitting or cutting means known to those having ordinary skill in the art. As a result of the slitting of the laminate through each wide elastic member 24, the SEEL 10 will have a continuous gasket zone 30, defined by the stretch edge 31, positioned along each lateral edge region 27, 29.

The invention encompasses various types of garments or absorbent articles in which a gasket zone 30 is present in the vicinity of any one or more garment openings. Depending on the garment, gasket zones 30 may encircle an entire garment opening or just a portion of the garment opening. Types of garments on which this invention can be used include personal care garments, such as diapers, training pants, absorbent underpants, adult incontinence products, certain feminine hygiene articles, and swim wear. The gasket zones 30 and elastic zones 20 may be used in similar fashion in medical garments including, for instance, medical gowns, caps, gloves, drapes, face masks, and the like, where it is desired to provide a gasket zone 30 in the vicinity of one or more garment openings without requiring a separately manufactured and attached elastic band. Further, the gasket zone 30 can be used around neck openings, arm openings, wrist openings, waist openings, leg openings, ankle openings, and any other opening surrounding a body part wherein fluid transfer resistance is desirable.

Figure 6:
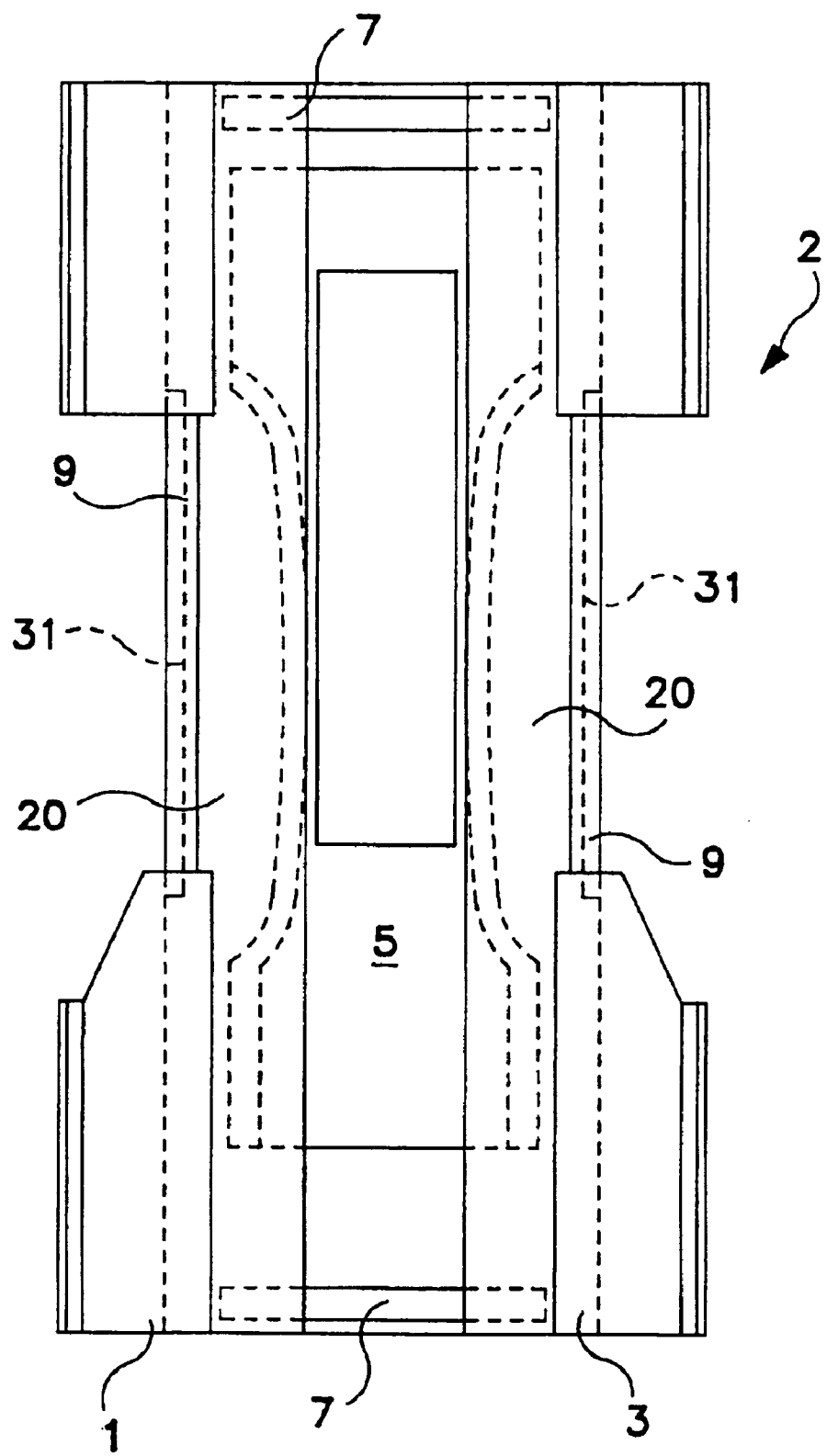
FIG. 6 is a schematic view of an exemplary pant-like absorbent article made of a SEEL material having at least one gasket zone and at least one elastic zone, in accordance with one embodiment of this invention.

For example, referring to FIG. 6, a pant-like absorbent garment 2, such as training pants, includes two side panels 1 and 3 made of a SEEL material. Waist elastic regions 7 and leg elastic regions 9 may contain gasket zones 30 while the remaining area of side panels 1 and 3 and/or chassis 5 may contain elastic zones 20. During use, the waist elastic regions 7 and the leg elastic regions 9 fit snugly against the wearer and effectively block most spillage of waste material which accumulates in chassis 5.

While the embodiments of the invention described herein are presently desired, various modifications and improvements can be made without departing from the spirit and scope of the invention. The scope of the invention is indicated in the appended claims, and all changes that fall within the meaning and range of equivalents are intended to be embraced therein.

What we claim is:

1. A stretch edge elastic laminate, comprising:
    a plurality of elastic filaments substantially aligned in a machine direction, each of the elastic filaments having a width-to-thickness ratio of less than about 2;
    a first nonwoven facing material bonded to a first side of the elastic filaments to form an elastic laminate zone; and
    at least one stretch edge positioned along a first lateral edge of the elastic laminate, the at least one stretch edge forming a first gasket zone, and including an elastic film or plug having a width-to-thickness ratio greater than about 5.

2. The stretch edge elastic laminate of claim 1, further comprising a second stretch edge positioned along an opposing second lateral edge of the elastic laminate, the second stretch edge forming a second gasket zone.

3. The stretch edge elastic laminate of claim 1, further comprising a second nonwoven facing material bonded to a second side of the elastic filaments.

4. The stretch edge elastic laminate of claim 1, wherein the stretch edge comprises an elastic film or plug substantially aligned in the machine direction, and a lateral edge region of the facing material bonded to the elastic film or plug.

5. The stretch edge elastic laminate of claim 4, wherein the first nonwoven facing material is attached to the elastic zone and the elastic film or plug using an elastic adhesive.

6. The stretch edge elastic laminate of claim 4, wherein the elastic film or plug has a thickness of about 0.003 inch to about 0.015 inch.

7. The stretch edge elastic laminate of claim 4, wherein the elastic film or plug has a width-to-thickness ratio of at least 10.

8. The stretch edge elastic laminate of claim 4, wherein the elastic film or plug has a width-to-thickness ratio of about 16 to about 78.

9. The stretch edge elastic laminate of claim 1, wherein the stretch edge has a width of about 0.078 inch to about 0.236 inch.

10. The stretch edge elastic laminate of claim 1, wherein each elastic filament has a width of about 0.011 inch to about 0.019 inch.

11. The stretch edge elastic laminate of claim 1, wherein each elastic filament has a thickness of about 0.011 inch to about 0.019 inch.

12. The stretch edge elastic laminate of claim 1, wherein the first gasket zone has a tension of about 80 g to about 250 g at 90% elongation of the first gasket zone.

13. The stretch edge elastic laminate of claim 1, wherein the elastic zone has a tension of at least about 40 g at 90% elongation of the elastic zone.

14. The stretch edge elastic laminate of claim 1, wherein the first gasket zone has a tension at least equal to a tension of the elastic zone.

15. A disposable garment comprising a stretch edge elastic laminate, the stretch edge elastic laminate comprising:
    at least one elastomeric layer including a plurality of elastomeric filaments in a central region of the elastomeric layer, each of the elastomeric filaments having a width-to-thickness ratio of less than about 2 and an elastic film or plug in at least one lateral edge region of the elastomeric layer, the elastic film or plug having a width-to-thickness ratio greater than about 5;
    a first facing material bonded to a first side of the elastomeric layer; and
    a second facing material bonded to a second side of the elastomeric layer,
    wherein a lateral edge of at least one elastic film or plug is aligned with a lateral edge of each of the first and second facing materials.

16. The disposable garment of claim 15, comprising a diaper.

17. The disposable garment of claim 15, comprising training pants.

18. The disposable garment of claim 15, comprising swim wear.

19. The disposable garment of claim 15, comprising absorbent underpants.

20. The disposable garment of claim 15, comprising a baby wipe.

21. The disposable garment of claim 15, comprising an adult incontinence product.

22. The disposable garment of claim 15, comprising a feminine hygiene product.

23. The disposable garment of claim 15, comprising a protective garment.

* * * * *